United States Patent [19]
Yazawa et al.

[11] Patent Number: 4,877,579
[45] Date of Patent: * Oct. 31, 1989

[54] MULTILAYER DEVICE FOR DETECTING BILURUBIN

[75] Inventors: Kenichiro Yazawa; Osamu Seshimoto; Masao Kitajima; Asaji Kondo, all of Saitama, Japan

[73] Assignee: Fuji Photo Film Co., Ltd., Kanagawa, Japan

[*] Notice: The portion of the term of this patent subsequent to Sep. 16, 2003 has been disclaimed.

[21] Appl. No.: 198,590

[22] Filed: May 23, 1988

Related U.S. Application Data

[63] Continuation of Ser. No. 842,748, Mar. 19, 1986, abandoned, which is a continuation of Ser. No. 542,569, Oct. 19, 1983, Pat. No. 4,612,290, which is a continuation of Ser. No. 294,278, Aug. 19, 1981, abandoned.

[30] Foreign Application Priority Data

Aug. 19, 1980 [JP] Japan .................................. 55-112998

[51] Int. Cl.[4] ............................................ G01N 33/72
[52] U.S. Cl. ......................................... 422/56; 422/57; 436/97; 436/170; 436/178
[58] Field of Search ........................ 422/56, 57, 58, 55; 436/97, 170, 178, 903

[56] References Cited

U.S. PATENT DOCUMENTS

| | | | |
|---|---|---|---|
| 4,069,016 | 1/1978 | Wu .................................. | 23/230 B |
| 4,069,017 | 1/1978 | Wu et al. ........................ | 422/56 X |
| 4,204,839 | 5/1980 | Wu et al. ........................ | 23/905 X |
| 4,260,579 | 4/1981 | Barton et al. ................... | 436/97 X |
| 4,292,272 | 9/1981 | Kitajima et al. ................ | 422/56 X |
| 4,303,408 | 12/1981 | Kim et al. ...................... | 422/57 X |
| 4,311,665 | 1/1982 | Wu .................................. | 23/905 X |
| 4,412,005 | 10/1983 | Wu .................................. | 436/97 |
| 4,612,290 | 9/1986 | Yazawa et al. ................. | 422/56 X |

Primary Examiner—Robert J. Hill, Jr.
Attorney, Agent, or Firm—Sughrue, Mion, Zinn, Macpeak & Seas

[57] ABSTRACT

A method for quantitative determination of bilirubin is disclosed. The method comprises bringing a bilirubin-containing aqueous liquid sample into contact with a hydrophobic bilirubin extracting composition containing a hydrophobic amine capable of extracting bilirubin. The amine extracts the bilirubin in said aqueous liquid sample. Photometry is then used to determine the concentration of bilirubin extracted with the bilirubin extracting composition. A device for use in this method is also disclosed. The device has a layer containing a hydrophobic bilirubin extracting composition containing a hydrophobic amine capable of extracting bilirubin.

20 Claims, 1 Drawing Sheet

MULTILAYER DEVICE FOR DETECTING BILURUBIN

This is a continuation of application Ser. No. 842,748, filed Mar. 19, 1986, now abandoned, which is a continuation of application Ser. No. 542,569, filed Oct. 19, 1983, now U.S. Pat. No. 4,612,290, which is a continuation of application Ser. No. 294,278, filed Aug. 19, 1981, now abandoned.

FIELD OF THE INVENTION

This invention relates to a method for determining the amount of bilirubin in an aqueous liquid sample, especially the body fluid of living organisms, and a device therefor.

BACKGROUND OF THE INVENTION

Bilirubin is the metabolic product of hemoglobin which is an oxygen carrier in blood. Determination of the amount of bilirubin in body fluid, especially blood, is important for detection of hemolysis and for checking liver function. One symptom of excess bilirubin in blood is jaundice. Determination of the bilirubin content in blood has been an important item of clinical chemical testing, and diazotization is the most common method of determination. In the diazotization method, bilirubin is coupled with a diazonium salt such as diazosulfanilic acid and the amount of the resulting colorant is measured in a spectrophotometer to estimate the bilirubin content. Details of the diazotization method are described in J. B. Landis and H. L. Pardue, *Clinical Chemistry*, 24 (10), 1690–1699 (1978).

Bilirubin is a yellow colorant which itself has an absorption peak at 435 nm or 465 nm and a molecular absorptivity coefficient of about $5 \times 10^4 C_{33}H_{36}O_6N_4$. In hospitals and other medical establishments it is common to measure the bilirubin content by direct colorimetry wherein a sample of blood serum is put in a capillary or cuvette and its color density is directly read. Using the absorption characteristics of bilirubin, this direct colorimetric technique is described in several publications such as U.S. Pat. No. 3,569,721. The technique is used advantageously in the diagnosis of jaundice in infants because there is no need to subtract a predetermined corrective value from the measured value, which in the case of samples of adult serum is interfered with by yellow colorants other than bilirubin.

In accordance with a known method, the bilirubin content is detected by examining the density of green color formed when bilirubin is oxidized by an oxidizer to biliverdin and by knowing precisely how this density is proportional to bilirubin content. This method is called the oxidation method, and is described in prior art references such as U.S. Pat. Nos. 3,348,920 and 3,607,093. The method is suitable for use in qualitative testing, but a modification adapted to semiquantitative determination has also been proposed. Whether it is adapted to qualitative or semiquantitative determination, the oxidation method is used in qualitative testing of urine necessary for diagnosis of high-conjugation bilirubinemia. For details of these methods for quantitative determination of bilirubin, see *Rinsho Kagaku Bunseki* (Analysis in Clinical Chemistry), ed. by Masayuki Saito, II, pp. 248–279. Since all of these methods use a reaction in solution, they are generally referred to as the "solution method".

Recently, various dry methods for determination of the bilirubin concentration have been proposed. According to one such method, an absorbent base such as filter paper is impregnated with a stabilized diazonium salt, and after drying, a sample of serum is spotted on the test paper to determine the amount of color formation. The determination of bilirubin content by this technique is disclosed in, for example, Japanese Patent Application (OPI) Nos. 60591/74 and 99091/74 (the symbol "OPI" as used herein means an unexamined published Japanese patent application). However, since the bilirubin content in the blood serum of a healthy subject is very small, less than 1 mg/dl, it has been difficult to achieve accurate determination of the bilirubin concentration using a paper type testing device.

However, this method achieves a quick and simple determination of the bilirubin content. Therefore, it has been generally used as a semiquantitative method for primary screening in emergency or group examination, as well as for grouping of suspects.

Japanese Patent Application (OPI) No. 89796/78 (corresponding to U.S. Pat. No. 4,069,017) discloses a method for the quantitative determination of bilirubin with a multilayer film for chemical analysis. In this method, techniques are utilized for mordanting bilirubin with a mordant composition and shifting the absorption wavelength and increasing the molecular absorptivity coefficient by at least 50%. Other techniques are useful for eliminating interference by substances other than the bilirubin and these techniques are combined with techniques for forming a uniform layer of the reagent on a film. This makes possible the uniform spreading of a sample solution by a spreading layer, and by so doing, the method achieves high accuracy analysis and sensitivity that has not been attainable by the paper type testing device described above.

Attempts to perform quick and simple determination while achieving high accuracy and sensitivity are also described in Japanese Patent Application (OPI) Nos. 89797/78 (corresponding to U.S. Pat. No. 4,069,016) and 24694/80 (corresponding to U.S. Pat. No. 4,204,839). The method disclosed in Japanese Patent Application (OPI) No. 89797/78 takes advantage of the ability of bilirubin to be bound firmly to albumin or the like. According to the theory of this method, a complex of colorant and albumin is formed on a hydrophilic binder, the molecule of the colorant is replaced by a free bilirubin in a sample solution and the colorant released is measured by spectrometry.

The method described in Japanese Patent Application (OPI) No. 24694/80 detects the bilirubin mordanted by a material similar to that described in Japanese Patent Application (OPI) No. 89796/78. However, it measures the intensity of fluorescence generated by bilirubin upon irradiation with excitation light, rather than measuring the color density in the region of its absorption wavelength. In the methods of Japanese Patent Application (OPI) Nos. 89796/78 and 24694/80, the mordanting of an interacting polymer mordant for bilirubin is essential. One problem in the application of the polymer mordant is that its mordant effect is easily lost since the active site (quaternary $N^\oplus$) is apt to be neutralized with an acid, activator or neutral salt during application of a coating solution and formation of other layers on the mordant layer. To solve this problem, acetone, alcohol and other organic solvents must be used as a solvent for the coating solution of polymer mordant. Furthermore, the use of an anionic activator, acid, or dissociative salt must be avoided in forming a radiation-blocking layer or other functional layers on the mordant layer. Placing a bilirubin-containing sample solution on a multilayer film for chemical analysis having the polymer mordant also has difficulties. Since the sample solution contains not only bilirubin but also many other substances that can be mordanted, competition between bilirubin and these substances for adsorption onto the mordant often results in low adsorption capacity and a false photometry. Another disadvantage exists in that the known multilayer films for chemical analysis are not adapted for use with whole blood, so serum must be separated from a sample of whole blood before it is subjected to analysis.

Japanese Patent Publication No. 28119/78 (corresponding to DT-OS 2,240,357) discloses a method for preparing a test paper for detection of bilirubin in the body fluid. The method is based on fact that addition of a phosphate diester as well as a diazonium salt accelerates the rate of color-forming reaction appreciably due to the binding of the diazonium salt to bilirubin.

The most accurate method for quantitative determination of bilirubin that has been used for many years relies on the colorimetric analysis of an isolate of bilirubin extracted from an aqueous solution with a hydrophobic organic solvent such as chloroform, benzene, carbon disulfide and chlorobenzene. This method uses the property of these organic solvents to dissolve bilirubin adequately so that it can separate easily from an aqueous liquid sample in layers upon standing after it is mixed with the sample. However, in view of the current demand for a quick and simple method of blood analysis that requires a minimum of blood sample and still provides accurate measurements, the method which relies on direct extraction of bilirubin from an aqueous solution and requires a fairly large amount of sample is not highly recommendable.

SUMMARY OF THE INVENTION

Therefore, we have made various efforts to develop a method for quantitative determination of bilirubin that meets the above-described practical requirements of clinical testing. This invention has been accomplished on the basis of our efforts and relates to a method and device for detecting bilirubin in body fluid (e.g., blood or serum). More specifically, this invention relates to a method for detecting bilirubin which comprises extracting bilirubin in a sample solution by bringing it into contact with a hydrophobic extracting solvent composition that contains at least one oil-soluble amine. The invention also relates to a device for carrying out this method. This invention is based on the finding that a composition containing a certain oil-soluble amine is capable of very efficiently extracting bilirubin from an aqueous solution.

DETAILED DESCRIPTION OF THE INVENTION

The device using the method of this invention is described below in detail. Quantitative determination of bilirubin in body fluid is very important in clinical testing and is performed fairly frequently during the chemical analysis of blood. The principle of the method of this invention is to extract bilirubin from a sample solution with a hydrophobic composition containing an oil-soluble amine. The method can be combined with known techniques. For instance, a bilirubin-containing sample solution can be mixed with the composition according to this invention. After the mixture is allowed to stand for a certain period so that the bilirubin is efficiently transferred into the composition, the content is determined by a known method for quantitative determination of bilirubin, such as direct colorimetry, diazotization, oxidation or fluorometry. In a particularly preferred embodiment, the method of this invention is combined with direct colorimetry.

The device for analysis of bilirubin according to this invention is most effective when used in the form of an integral multilayer sheet. As described in the above referred to publications, integral multilayer devices for chemical analysis include a novel dry analytical device capable of determining the concentration of an intended substance in body fluid simply by spotting a very small amount of a sample of body fluid (usually in 5 to 20 $\mu$l) on the surface of the analytical device. Specific examples of such integral multilayer device for analysis of bilirubin are described in Japanese Patent Application (OPI) Nos. 89796/78, 89797/78 and 246943/78, and other patents.

Figure 3:
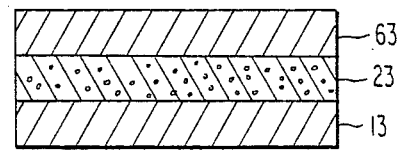
FIG. 3 is a cross-sectional view of a three-layer embodiment of the present invention.

One specific embodiment of the device for analysis of bilirubin according to the present invention is schematically represented in FIG. 3. The device is comprised of a light-transmitting, water-impermeable support 13 which is overlaid with an extracting layer 23 wherein a hydrophobic extracting solvent composition containing an oil-soluble hydrophobic amine is dispersed in a hydrophilic binder. The extracting layer is overlaid with a spreading layer 63 impregnated with a bilirubin dissociating agent from conjugated protein. In this integral multilayer device, when a sample of aqueous solution containing bilirubin is spotted on the device, the solution is spread uniformly in such a manner that a substantially constant amount penetrates the spreading layer and moves toward the underlying extracting layer. At the same time, the dissociating agent acts on the solution to provide a diffusible, free form of bilirubin. As the sample solution goes into the extracting layer, the bilirubin to be detected is extracted and concentrated with the hydrophobic extracting solvent composition containing an oil-soluble hydrophobic amine. After incubation for a given period under given conditions, the amount of bilirubin concentrated in the extracting layer is measured by photometry with reflected or transmitting light. The bilirubin content of the sample solution can be determined from the calibration curve drawn by using a sample of a known bilirubin concentration.

The components of the device used in the method of this invention are described more specifically below. The bilirubin extracting composition for use in this invention is a hydrophobic liquid composition containing a primary, secondary or tertiary amine. The composition is "hydrophobic" to such an extent that it is capable of forming at least an emulsion when it is dispersed in neutral water. The term "hydrophobic" does not mean that the composition has no solubility in water. The composition is "liquid" at the incubation temperature. The incubation temperature varies with the design of the analytical device and it is usually between about 10° and about 50° C., the most commonly used range being from about 25° to about 40° C.

The hydrophobic organic amine used in the device of this invention may be primary, secondary or tertiary, and it may be a substituted or unsubstituted chain alkyl- or alkenyl-amine, aromatic or alicyclic alkylamine, or substituted or unsubstituted cyclic amine or substituted heterocyclic amine. Illustrative hydrophobic amines include primary amines such as heptylamine, octylamine and nonylamine; secondary amines such as dicyclohexylamine, benzylmethylamine, and (trialkylmethyl)long-chain secondary amines (such as, for example, lauryl(tributylmethyl)amine, and dodecenyl(tributylmethyl)amine); and tertiary amines such as p-methyl-N,N-diethylaniline, benzyldimethylamine, N-phenylmorpholine, dioctylmethylamine, and trioctylamine. Laurylamine, tribenzylamine, heptadecylamine, bis[p-(dimethylamino)phenyl]methane, and other amines which are solid at room temperature can be used in this invention if they are dissolved in a hydrophobic oil which works as an extraction aid.

These amines are mixed with or dissolved in an extraction aid which is a stable, hydrophobic, high-boiling organic or inorganic liquid material. Illustrative extraction aids that are effectively used in this invention include a phthalic acid derivative such as dibutyl phthalate or dioctyl phthalate; an organic phosphorus compound such as triphenyl phosphate, tricyclohexyl phosphate, trioctyl phosphate or tributoxyethyl phosphine oxide; an adipate such as dibutyl adipate; chlorinated or alkyl-substituted diphenyl or triphenyl or alkyl-substituted diphenylethane; and an alkylamide such as N,N-dimethyllaurylamide, N,N-diethyllaurylamide or N,N-dimethylnonylamide.

Most of these oils used as extraction aids have a very low solubility in bilirubin. However, they are effective in enhancing the extracting ability of the amines with which they are mixed. Alkylamides and organic phosphorus compounds are effective for use in the practice of this invention. We have found that when they are mixed with the hydrophobic amine, they not only form a good extracting composition but exhibit "synergetic" effect. Particularly effective alkylamides include N,N-dimethyllaurylamide, N,N-diethyllaurylamide and N,N-dimethylnonylamide. Organic phosphorus compounds such as tricyclohexyl phosphate, trioctyl phosphate and tributoxyethyl phosphine oxide are also extracting aids which have synergetic effect. The combination of organic amine and extracting aid that achieves particularly effective extraction is a composition containing a (trialkylmethyl)long-chain secondary amine, illustrative examples of which are the combination of dodecenyl(tributylmethyl)amine and dimethyllaurylamide and that of lauryl(tributylmethyl)amine and diethyllaurylamide. A specific example of the synergetic effect is set forth below. N,N-diethyllaurylamide is a liquid substance that has little ability to extract bilirubin from bilirubin-containing blood serum. However, a hydrophobic extracting solvent composition wherein the amide is mixed with dodecenyl(tributylmethyl)amine at a volume ratio of 1:1 is capable of extracting bilirubin in an amount of at least twice that of the amount extracted by the amine alone.

In a specific embodiment of the process of this invention, a known bilirubin detecting reagent is incorporated in the above-described hydrophobic extracting solvent composition, and the amount of the reaction product of the extracted bilirubin and the reagent is determined by colorimetry and other suitable methods. Examples of the bilirubin detecting reagent include a diazonium compound, halogenated (or alkoxy)-benzenediazonium salt and long-chain alkoxycarbonyl substituted benzenediazonium salt that form a color upon reaction with bilirubin. Highly oil-soluble diazonium salts such as 2-chloro-5-hexadecyloxycarbonylbenzenediazonium and 2-methoxy-5-tetradecyloxycarbonylbenzenediazonium are particularly effective for use in this invention.

The hydrophobic extracting solvent composition used in the testing device of this invention may optionally contain a pH indicator, reagent, acid, alkali, salt or polymer. An oily product is produced by dissolving the oil-soluble amine in a solution which has an organic solvent-soluble polymer dissolved in an organic solvent substantially immiscible with water. Examples of such polymer include cellulose diacetate, cellulose triacetate, cellulose acetate propionate, ethyl cellulose, methyl methacrylate, polystyrene, and bisphenol A polycarbonate.

In the integral multilayer device for chemical analysis, microfine particles of the hydrophobic extracting solvent composition according to this invention are dispersed in a hydrophilic binder. The size of the microfine particles is in the range of from about 0.01 $\mu$m to about 20 $\mu$m, preferably from about 0.1 to about 10 $\mu$m. The hydrophobic microfine particles are such that the greater part of the components of the composition are contained in individual particles which are impermeable to water.

The hydrophilic binders used in the extracting layer that contains the hydrophobic extracting solvent composition are water-soluble polymeric substances such as water-soluble protein (e.g., gelatin, albumin and collagen), plant gum (e.g., agar, sodium alginate, and agarose), and synthetic polymers such as olefin, maleic anhydride copolymer, polyvinyl alcohol, polyvinyl pyrrolidone, polyacrylamide and poly(sodium vinyl benzensulfonate). These substances are capable of forming a film that has grains of the hydrophobic extracting solvent composition contained therein, and after drying, it becomes highly permeable to an aqueous sample solution containing bilirubin. It is to be understood that the hydrophilic binder may contain a pH indicator and other reagents for various purposes.

The spreading layer in the integral multilayer device for chemical analysis may be made of a non-fibrous, isotropic porous material of the type described in the above referred to publications. Alternatively, it may be made of a hydrophilic fabric. Examples of the non-fibrous, isotropic porous material include a brush polymer (also called membrane filter), a material having a microporous substance such as diatomaceous earth or microcrystalline substance (e.g., microcrystalline cellulose) dispersed uniformly in a binder; a porous material in which microspherical beads of glass or synthetic polymeric substance that are place in point-contact relationship with each other are retained in a binder; and a brush polymer having microfine particles of compounds such as $TiO_2$ and $BaSO_4$ dispersed therein uniformly. Examples of hydrophilic fabrics include a fabric that has been thoroughly washed with water, degreased and dried and a fabric that has been washed with water, degreased and impregnated with a small amount of a surfactant, lubricant, or a hydrophilic polymer that optionally contains fine particles of $TiO_2$ or $BaSO_4$. For details of the technique for using the hydrophilic fabric as the spreading layer and the fabric itself, see Japanese Patent Application No. 72047/79 (corresponding to GB 2,052,057 A). The hydrophilic fabric can be used in this invention in compliance with the teaching of the patent.

When the spreading layer is made of a non-fibrous, isotropic porous material, its thickness is generally in the range of from about 50 to about 500 μm, preferably from about 80 to about 300 μm. When the layer is made of a hydrophilic fabric, its thickness is generally in the range from about 80 μm to about 1 mm, preferably from about 100 μm to about 400 μm in terms of the thickness of a hydrophilic fabric that has been dried under natural conditions.

A spreading layer made of a non-fibrous, isotropic porous material can be formed on the layer of a reagent by a method such as described in Japanese Patent Application (OPI) Nos. 53888/74 (corresponding to U.S. Pat. No. 3,992,158) and 137192/75 (corresponding to U.S. Pat. No. 3,977,568). According to this method, a solution or dispersion capable of forming a non-fibrous, isotropic porous material is spread and dried on the layer of reagent or a thin layer of non-fibrous, isotropic porous material is bonded to the layer of reagent. A spreading layer made of a hydrophilic fabric can be formed on the layer of reagent by bonding the fabric onto the reagent layer. The spreading layer may contain various reagents depending on the need. Particularly important reagents for the practice of this invention include a bilirubin dissociating agent, surfactant, pH modifier and oxidizing agent.

There are two types of bilirubin; direct bilirubin and indirect bilirubin, in the body fluid. Both types are bound to albumin, a proteinaceous material, and hence are very slow in diffusing through a film of a hydrophilic binder. However, the diffusion and penetration of bilirubin is essential in the integral multilayer device for chemical analysis of bilirubin. When a reference serum containing bilirubin is spotted on an untreated spreading layer, bilirubin, most of which is non-diffusible, is not extracted in the extracting layer at all. This problem is solved by incorporating in the spreading layer a dissociating agent that cuts the bond between bilirubin and albumin to provide a free form of bilirubin. Many compounds are known as such bilirubin dissociating agents, and caffeine-sodium benzoate, dyphylline and surfactant have been found to be effective in the practice of this invention. Caffeine-sodium benzoate has long been used as a bilirubin dissociating agent and is particularly effective in this invention. Its dissociating action is further enhanced in the presence of sodium acetate or EDTA. Surfactants that are effective in the practice of this invention are octylphenoxypolyethoxyethanol, ictenone A and B.

These dissociating agents are desirably contained in the spreading layer. However, a layer of dissociating agents may be formed under the spreading layer. Greater dissociating effect is often achieved by placing the dissociating agent in other layers, such as a radiation-blocking layer, a light-reflecting layer, a layer to prevent hemoglobin diffusion or an adhesive layer, that are disposed as required. It is necessary that the spreading layer contains a sufficient amount of dissociating agent to completely dissociate all bilirubin in the sample solution. A large amount of solid such as dissociating agent contained in the spreading layer clogs pores in the spreading layer, and as a result, free spreading of the sample solution in the spreading layer is inhibited. Impregnation with the dissociative agent causes a significant change in the affinity of surface of the spreading layer for water. As a consequence of this change, free spreading and penetration of the sample solution is inhibited. For instance, a spreading layer made of a non-fibrous porous membrane (e.g., Fuji Microfilter FM-500 of Fuji Photo Film Co., Ltd.) permits normal free spreading of a sample solution. However, if it is impregnated with about 5 g/m$^2$ of a dissociating agent (i.e., caffeine-sodium benzoate), the spreading of the sample soluton is inhibited to such an extent that a quantitative determination of the intended substance becomes impossible. Furthermore, impregnation of the spreading layer with a dissociating agent after the layer is formed on a multilayer film is not good because it causes precipitation of the dissociating agent and other problems. A more practical method would be to laminate an underlying layer with a spreading layer impregnated with the dissociating agent. However, when using this method, if the content of the dissociating agent is increased, poor adhesion to the underlying layer often causes peeling or uneven spreading of the sample solution. In consideration of these facts, a spreading layer that best suits this invention is obtained by laminating a coating film with a cloth (fabric) impregnated with a dissociating agent. A cloth which is particularly advantageous has a porosity and mechanical strength so high that not only can it be impregnated with a large amount of dissociating agent but its spreading characteristics are least affected by external conditions. The cloth can be impregnated with up to about 100 g/m$^2$ of dissociating agent. The spreading layer is formed as a laminate to cover the surface of the coating film.

The normal concentration of bilirubin in blood is less than 1 mg/dl. Since a sample with a small bilirubin content permits a correspondingly small amount of bilirubin to be extracted, easy detection requires a maximum amount of sample solution to be supplied per given area of the testing device.

The light-transmitting, water-impermeable support in the integral multilayer device for chemical analysis according to this invention is made of a known transparent support such as a plastic film, for example, polyethylene terephthalate, cellulose ester (cellulose diacetate, cellulose triacetate, or cellulose acetate propionate), polycarbonate or polymethyl methacrylate, or a glass sheet. The support has a thickness of from about 50 μm to about 2 mm. If the support is hydrophobic and does not have firm adhesion to the hydrophilic binder in the extracting layer, it may be subjected to a known surface treatment. Examples of such treatments involve making the surface of the support hydrophilic (e.g., irradiation with ultraviolet rays, electron beams, flame treatment, or hydrolysis with alkali), or priming the surface of the support with a substance having suitable adhesion to both the support and the hydrophilic binder in the extracting layer, or forming fine projections and recesses (by brushing, electroetching, etc.) on the surface of the support in such a manner that they do not decrease the light transmittance of the support significantly.

A spreading layer made of a non-fibrous, isotropic porous material or a hydrophilic fabric is bonded to the extracting layer by using the properties of the hydrophilic binder polymer in the extracting layer. While the extracting layer is not completely dry, or after wetting the surface of a dry extracting layer with water which may or may not contain a surfactant, the non-fibrous, isotropic porous material or hydrophilic fabric is brought into intimate contact with the surface of the extracting layer, with suitable pressure being applied as required. The non-fibrous, isotropic porous material or hydrophilic fabric may also be bonded to the extracting layer either by using an adhesive permeable to the sample solution or by forming on the extracting layer an adhesive layer (to be described hereunder) permeable to an aqueous sample solution.

If necessary, the integral multilayer device for chemical analysis according to this invention may further include a reagent layer, a detection layer or a barrier layer. Details of these layers are given in the aforementioned patents and a desired layer may be formed in compliance with the teachings thereof. The integral multilayer device for chemical analysis according to this invention may also include a radiation-blocking layer or light-reflecting layer between the extracting layer and the spreading layer. Furthermore, an adhesive layer permeable to the aqueous liquid sample that provides firm adhesion to the spreading layer may be formed between the spreading layer and extracting layer or radiation-blocking layer or light-refelcting layer. Details of the radiation-blocking layer, light-reflecting layer and adhesive layer are also given in the aforementioned patents and a desired layer may be formed in compliance with the teachings thereof.

The radiation-blocking layer or light-reflecting layer is made of white microfine particles of $TiO_2$, $BaSO_4$, etc., that are dispersed in a hydrophilic binder polymer. The thickness of these layers is generally in the range of from about 1 $\mu m$ to about 50 $\mu m$, preferably from about 2 $\mu m$ to about 20 $\mu m$. A layer made of fine particles of a compound having a white or pale metallic gloss such as aluminum dispersed in a hydrophilic binder polymer may be formed in a thickness of from about 2 to about 50 $\mu m$, preferably from about 3 to about 20 $\mu m$. Alternatively, a thin porous metallic layer permeable to the aqueous liquid sample may be formed of a white or pale colored metal such as aluminum in a thickness of from about 5 $\mu m$ to about 100 $\mu m$, preferably from about 5 $\mu m$ to about 50 $\mu m$.

The adhesive layer may be made of a polymer of the same kind as thatof the aqueous liquid sample-permeable, hydrophilic polymer used as a binder in the extracting layer, radiation-blocking layer or light-reflecting layer. The thickness of the adhesive layer is generally in the range of from about 0.5 to about 10 $\mu m$, preferably from about 0.7 $\mu m$ to about 5 $\mu m$. The spreading layer can be bonded to the adhesive layer made of a hydrophilic polymer in the manner described below. An aqueous solution of hydrophilic polymer is spread on the extracting layer, radiation-blocking layer or light-reflecting layer, and before the coating is completely dry, or after wetting the surface of a dry coating with water which may or may not contain a surfactant, the non-fibrous, isotropic porous material or the hydrophilic fabric is placed in contact with the surface of the resulting adhesive layer under suitable pressure. Accordingly, a uniform coating of the spreading layer can be bonded to the adhesive layer. An integral multilayer device for chemical analysis wherein the spreading layer is firmly bonded to the adhesive layer can also be obtained by spreading, on the adhesive layer, a solution or dispersion capable of forming a non-fibrous, isotropic porous layer.

For the practice of this invention, a layer may be formed so that hemoglobin that is the most obstructive to the analysis of bilirubin will not be diffused into the extracting layer. Such layer preferably has a thickness of from about 1 to about 10 $\mu m$. Interference by hemoglobin always presents a big problem in quantitative determination ofbilirubin. In this invention, this problem is solved almost completely by forming such layer made of a hydrophilic polymer (e.g., gelatin, polyvinyl alcohol or carboxymethyl cellulose) between the spreading layer and extracting layer. The underlying principle is that the diffusibility of hemoglobin in the layer of hydrophilic polymer is very low, whereas the diffusion of dissociated bilirubin is not obstructed by the polymer layer significantly. Another advantage of the method of this invention is that it is capable of eliminating the detrimental effect of "chyle serum" that is in the form of an emulsion of free fats. Diffusion of the emulsified fats into the extracting layer is completely prevented by this layer.

Figure 1:
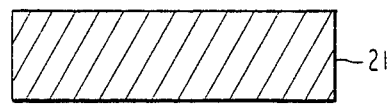
FIG. 1 is a cross-sectional view of the single layer embodiment of the present invention showing the layer containing a hydrophobic bilirubin extracting composition.

Specific embodiments of the testing device according to this invention are hereunder described by reference to the accompanying drawings. FIG. 1 is a schematic representation of the device in a sheet form 21 which comprises a porous support such as filter paper, porous membrane or cloth at least the surface of which is hydrophilic is impregnated with a hydrophobic extracting solvent composition containing at least one oil-soluble amine according to the feature of this invention. A sample solution containing bilirubin is spotted on the device or the device is immersed in the solution under given conditions, and amount of the bilirubin extracted is determined.

Figure 2:
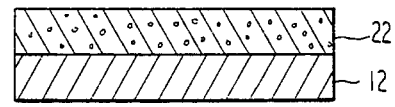
FIG. 2 is a cross-sectional view of a two-layer embodiment of the present invention.

FIG. 2 shows a device wherein a water-impermeable support 12 is coated with an extracting layer 22 wherein the hydrophobic extracting solvent composition of this invention is dispersed in a hydrophilic binder.

FIG. 3 shows an integral multilayer device which comprises a water-impermeable support 13 that is coated with an extracting layer 22 which is further coated with a spreading layer 63.

Figure 4:
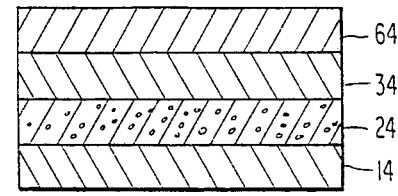
FIG. 4 is a cross-sectional view of a four-layer embodiment of the present invention.

FIG. 4 shows an integral multilayer device which comprises a water-impermeable support 14 that is coated with an extracting layer 24, a radiation-blocking layer 34 and a spreading layer 64 in that order.

Figure 5:
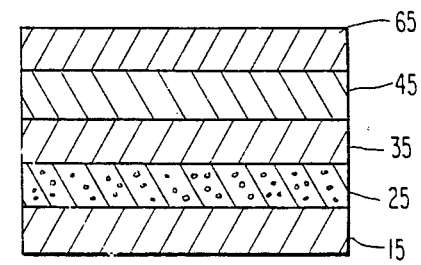
FIG. 5 is a cross-sectional view of a five-layer embodiment of the present invention.

FIG. 5 shows a device which comprises a water-impermeable support 15 that is coated with an extracting layer 25, a radiation-blocking layer 35, a layer 45 which prevents the diffusion of hemoglobin into the extracting layer, and a spreading layer 65 in that order.

This invention is now described in greater detail by reference to the following examples which are given here for illustrative purposes only and are by no means intended to limit the scope of this invention.

EXAMPLE 1

A hydrophobic extracting solvent composition was prepared by mixing 5 g of dodecenyl(trialkylmethyl)amine (liquid ion exchanger LA-1 of Rohm and Haas Co.) with 5 g of N,N-dimethyllaurylamide. A 0.5 ml sample of a control serum (Versatol A, alternate) containing 2.7 mg/dl of bilirubin was put in a test tube, and it was mixed with 4.5 ml of physiological saline and 2 ml of the hydrophobic extracting solvent composition under stirring. After standing for 30 minutes, the oily layer was separated from the aqueous layer, and its optical density at 550 nm was measured with a spectrophotometer. About 92% of the bilirubin in the aqueous layer was found to have been extracted with the hydrophobic extracting solvent composition.

EXAMPLE 2

A hydrophobic extracting solvent composition was prepared by dissolving 1.75 g of dodecenyl(trialkylmethyl)amine (liquid ion exchanger LA-1 of Rohm and Haas Co.) in 1.75 g of N,N-diethyllaurylamide. A solution of hydrophilic reagent was prepared by dissolving 300 mg of ethylenediaminetetraacetic acid tetrasodium salt (EDTA4Na) and 175 mg of glycerine in 525 g of a 6 wt% aqueous solution of gelatin. An O/W emulsion was prepared by dispersing the hydrophobic extracting solvent composition in the solution of hydrophilic reagent with a homogenizer according to the conventional method. The hydrophobic grains containing dodecenyl(trialkylmethyl)amine had a uniform size of less than 2 $\mu$m. The emulsion was spread on a primed transparent polyethylene terephthalate (PET) film 185 $\mu$m thick and dried to make a bilirubin extracting layer. The thickness of the dry layer was about 20 $\mu$m. A microscopic observation of the extracting layer showed that it had fine oil globules dispersed in the gelatin layer.

The resulting product was cut into small pieces (5×20 mm) which were immersed for 15 minutes in 7% albumin having bilirubin in different concentrations, and the varying color intensity due to the bilirubin extracted was determined. The color intensity was increased in substantial proportion to the concentration of bilirubin in the range of from 2 to 50 mg/dl.

EXAMPLE 3

Filter paper (Product No. 7 of Toyo Roshi Kaisha Ltd.) was impregnated with an aqueous solution comprising 44 g of caffeine, 72 g of anhydrous sodium benzoate, 82 g of anhydrous sodium acetate and 1,000 g of water, and the resulting paper contained solids in an amount of 10 g/m$^2$. Three discs (dia. of about 8 mm) were cut from the filter paper and placed on the extracting layer of a testing device prepared as in Example 2. Ten microliters each of control serum having bilirubin concentrations of 2.7 mg/dl, 5.5 mg/dl and 19 mg/dl was spotted on the discs, and after heating at 37° C. for 10 minutes, the optical density (OD$_R$) at 450 nm was measured with a reflection densitometer. The OD value was proportional to the bilirubin concentration.

EXAMPLE 4

A hydrophobic extracting solvent composition was prepared by dissolving 1.75 g of dicyclohexylamine (product of Wako Pure Chemical Industries, Ltd.) in 1.75 g of N,N-dimethyllaurylamide. A solution of hydrophilic reagent was prepared by dissolving 300 mg of EDTA4Na and 175 g of glycerine in 525 g of 6 wt% aqueous gelatin solution. An O/W emulsion was prepared by dispersing the hydrophobic extracting solvent composition in the solution of hydrophilic reagent with a homogenizer according to the conventional method. The hydrophobic grains containing dicyclohexylamine had a uniform size of less than 2 $\mu$m. The emulsion was spread on a primed transparent PET film 185 $\mu$m thick and dried to make a bilirubin extracting layer. The thickness of the dry layer was about 20 $\mu$m. A microscopic observation of the extracting layer showed that it had fine oil globules dispersed in the gelatin layer.

The emulsion layer was wet with water, and a microfilter (FM-500 of Fuji Photo Film Co., Ltd.) was pressed against the emulsion layer to form a spreading layer. The resulting product was subjected to photometry as in Example 3, giving the same results as in Example 3.

EXAMPLE 5

A hydrophobic extracting solvent composition was prepared by dissolving 1.75 of dodecyl(trialkylmethyl)amine (liquid ion exchanger LA-2 of Rohm and Haas) in 1.75 g of N,N-diethyllaurylamide. A solution of hydrophilic agent was prepared by dissolving 300 mg of EDTA4Na and 175 mg of glycerine in 525 g of a 6 wt% aqueous solution of gelatin. An O/W emulsion was prepared by dispersing the hydrophobic extracting solvent composition in the solution of hydrophilic reagent with a homogenizer in the conventional manner. The hydrophobic grains containing dodecyl(trialkylmethyl)amine had a uniform size of less than 2 $\mu$m. The emulsion was spread on a primed transparent PET film 185 $\mu$m thick and dried to make a bilirubin extracting layer. The thickness of the dry layer was about 20 $\mu$m. A microscopic observation of the extracting layer showed that it had fine oil globules dispersed in the gelatin layer.

A 5 wt% aqueous solution containing 35 wt% of fine titanium dioxide grains was spread on the emulsion layer and dried to form a radiation-blocking layer 15 $\mu$m thick. A 5% aqueous gelatin solution was spread on the radiation-blocking layer and dried to form an adhesive layer 3 $\mu$m thick.

(a) A solution of 66 g of caffeine, 108 g of anhydrous sodium benzoate, 123 g of anyhydrous sodium acetate, and 1000 g of water was mixed with 150 g of 10% aqueous gelatin solution and 20 g of 1% Triton X-100 (product of Rohm and Haas Co.) to make a uniform solution. A cotton velvet (Product No. 22000 of Kanebo Ltd.) was impregnated with the solution. The velvet contained 30 g/m$^2$ of the solution on a dry basis. The surface of the adhesive layer was wet with water, and the cotton velvet was pressed onto the titanium dioxide layer to make a spreading layer. A 10 $\mu$l sample of reference bilirubin prepared from the aqueous bilirubin solution of Warner-Lambert Co. was spotted on the spreading layer and heated at 37° C. for 10 minutes. The optical density (OD$_R$) at 450 nm was measured with a reflection densitometer. The data showing the difference ($\Delta$OD$_R$) between the optical densities obtained with the testing device of this invention and those obtained with a phosphate buffer solution (pH=7.3) of 4% bovine albumin is given in Table 1 below.

TABLE 1

| Total Bilirubin (mg/dl) | 0.5 | 1.7 | 2.8 | 5.1 | 7.4 | 9.8 | 14.4 | 19 |
|---|---|---|---|---|---|---|---|---|
| $\Delta$OD$_R$ | 0.014 | 0.059 | 0.109 | 0.190 | 0.264 | 0.329 | 0.404 | 0.506 |

(b) Sheets of filter paper (dia.=6 mm) treated as in Example 3 were laminated on a multilayer testing device consisting of a PET base, extracting layer and a radiation-blocking (TiO$_2$) layer. Ten microliters each of control serum (DADE) having bilirubin concentrations of 1.2 mg/dl, 4.5 mg/dl and 11 mg/dl was spotted on the respective discs and heated at 37° C. for 10 minutes, and the reflection density (OD$_R$) was measured. The data showing the difference ($\Delta$OD$_R$) between the optical densities obtained with the testing device of this invention and those obtained with buffered albumin is given in Table 2 below.

TABLE 2

| Bilirubin Concentration (mg/dl) | 1.2 | 4.5 | 11 |
|---|---|---|---|
| $\Delta OD_R$ | 0.12 | 0.30 | 0.55 |

EXAMPLE 6

A hydrophobic extracting solvent composition was prepared by dissolving 1.75 g of dodecyl(trialkylmethyl)amine (liquid ion exchanger LA-2 of Rohm and Haas Co.) in 1.75 g of N,N-dimethyllaurylamide. A solution of hydrophilic reagent was prepared by dissolving 300 mg of EDTA4Na and 175 mg of glycerine in 525 g of a 6 wt% aqueous gelatin solution. An O/W emulsion was prepared by dispersing the hydrophobic extracting solvent composition in the solution of hydrophilic reagent with a homogenizer by the conventional method. The hydrophobic grains containing dodecyl(trialkylmethyl)amine had a uniform size of less than 2 μm. The emulsion was spread on a primed transparent PET film 185 μm thick and dried to make a bilirubin extracting layer. The thickness of the dry layer was about 20 μm. A microscopic observation of the layer showed that it had fine oil globules dispersed in the gelatin layer. A radiation-blocking layer and an adhesive layer were formed as in Example 5, except that a layer to prevent hemoglobin diffusion (3 μm) was formed between the two layers by spreading and drying a 5 wt% aqueous solution of polyvinyl alcohol. A 10 μl of a whole blood sample hemolyzed with 0.1% of saponin was spotted on the testing device at 37° C. for 10 minutes. No interference by hemoglobin occurred.

While the invention has been described in detail and with reference to specific embodiments thereof, it will be apparent to one skilled in the art that various changes and modifications can be made therein without departing from the spirit and scope thereof.

What is claimed is:

1. An integral multilayer device for quantitatively determining the amount of bilirubin in an aqueous liquid sample comprising the following elements:
   (1) a light-transmitting, water-impermeable support,
   (2) an indicator layer containing a bilirubin extracting composition dispersed in a film-forming hydrophilic polymer binder, and (3) a porous spreading layer, wherein elements (1) to (3) are present in the recited order with respect to each other, said bilirubin extracting composition is hydrophobic to such an extent that it forms at least an emulsion when it is dispersed in neutral water and comprises a hydrophobic oil-soluble primary, secondary or tertiary amine capable of extracting bilirubin and an extraction aid, and wherein a dissociating agent for bilirubin is incorporated into the spreading layer or a further layer (4) between the porous spreading layer and (3) the layer containing the bilirubin extracting composition (2) in an amount sufficient to completely dissociate all bilirubin in a sample, said layers being in sequence and layer (2) overlays (1) and is in direct contact therewith.

2. The device for quantitatively determining the amount of bilirubin in an aqueous liquid sample as claimed in claim 1, wherein said bilirubin extracting composition is liquid at the incubation temperature at which bilirubin is extracted which is in the range of about 10° C. to about 50° C.

3. The device for quantitatively determining the amount of bilirubin in an aqueous liquid sample as claimed in claim 2, wherein the incubation temperature is in the range of from about 25° C. to about 45° C.

4. The device for quantitatively determining the amount of bilirubin in an aqueous liquid sample as claimed in claim 1, wherein said hydrophobic oil-soluble amine is selected from the group consisting of heptylamine, octylamine, nonylamine, dicyclohexylamine, benzylmethylamine, lauryl(tributylmethyl)amine, dodecenyl(tributylmethyl)amine, p-methyl-N,N-diethylaniline, benzyldimethylamine, N-phenylmorpholine, dioctylmethylamine and trioctylamine.

5. The device for quantitatively determining the amount of bilirubin in an aqueous liquid sample as claimed in claim 1, wherein said extraction aid is selected from the group consisting of dibutyl phthalate, dioctyl phthalate, triphenyl phosphate, tricyclohexyl phosphate, trioctyl phosphate, tributoxyethyl phosphine oxide, chlorinated or alkyl-substituted diphenyl or triphenyl or alkyl-substituted diphenylethane, N,N-dimethyllaurylamide, N,N-diethyllaurylamide and N,N-dimethylnonylamide.

6. The device claimed in claim 1, wherein said device has a single layer containing said bilirubin extracting composition.

7. The device for quantitatively determining the amount of bilirubin in an aqueous liquid sample as claimed in claim 1, which further comprises a layer which prevents diffusion of hemoglobin between the porous spreading layer (3) and the bilirubin extracting layer (2).

8. The device for quantitatively determining the amount of bilirubin in an aqueous liquid sample as claimed in claim 1, wherein the device includes the further layer (4) between the porous spreading layer (3) and the layer containing the bilirubin extracting composition (2) and wherein the further layer (4) is selected from the group consisting of a dissociating agent layer, a radiation-blocking layer, a light-reflecting layer, a layer to prevent hemoglobin diffusion and an adhesive layer.

9. The device for quantitatively determining the amount of bilirubin in an aqueous liquid sample as claimed in claim 1 which further comprises a layer which prevents diffusion of hemoglobin between the porous spreading layer (3) and the bilirubin extracting layer (2).

10. The device for quantitatively determining the amount of bilirubin in an aqueous liquid sample as claimed in claim 1, wherein said dissociating agent is selected from the group consisting of caffeine-sodium benzoate, dyphylline and a surfactant.

11. The device for quantitatively determining the amount of bilirubin in an aqueous liquid sample as claimed in claim 1, wherein said dissociating agent is octylphenoxypolyethoxyethanol.

12. The device for quantitatively determining the amount of bilirubin in an aqueous liquid sample as claimed in claim 1, wherein said dissociating agent is caffeine-sodium benzoate in combination with sodium acetate or ethylenediamine tetraacetic acid.

13. A device for quantitatively determining the amount of bilirubin in an aqueous liquid sample comprising:

an indicator layer which includes a hydrophobic bilirubin extracting composition, wherein the bilirubin extracting composition comprises a hydrophobic oil-soluble primary, secondary or tertiary amine capable of extracting bilirubin and an extraction aid, said bilirubin extracting composition being hydrophobic to such an extent that it forms at least an emulsion when it is dispsered in neutral water and wherein said device has a single layer containing said bilirubin extracting composition, there being present a dissociating agent for bilirubin in a layer above the indicator layer in an amount sufficient to completely dissociate all bilirubin in a sample and wherein the device includes a light-transmitting, water-impermeable support with the indicator layer overlaying the support and being in direct contact therewith.

14. The device claimed in claim 13, wherein said bilirubin extracting composition is liquid at the incubation temperature at which bilirubin is extracted which is in the range of from about 10° C. to about 50° C.

15. The device claimed in claim 14, wherein said incubation temperature is in the range of from about 25° C. to about 45° C.

16. The device for quantitatively determining the amount of bilirubin in an aqueous liquid sample as claimed in claim 13, wherein said hydrophobic oil-soluble amine is selected from the group consisting of heptylamine, octylamine, nonylamine, dicyclohexylamine, benzylmethylamine, lauryl(tributylmethyl)amine, dodecenyl(tributylmethyl)amine, p-methyl-N,N-diethylaniline, benzyldimethylamine, N-phenylmorpholine, dioctylmethylamine and trioctylamine.

17. The device for quantitatively determining the amount of bilirubin in an aqueous liquid sample as claimed in claim 13, wherein said extraction aid is selected from the group consisting of dibutyl phthalate, dioctyl phthalate, triphenyl phosphate, tricyclohexyl phosphate, trioctyl phosphate, tributoxyethyl phosphine oxide, chlorinated or alkyl-substituted diphenyl or triphenyl or alkyl-substituted diphenylethane, N,N-dimethyllaurylamide, N,N-diethyllaurylamide and N,N-dimethylnonylamide.

18. An integral multilayer device for quantitatively determining the amount of bilirubin in an aqueous liquid sample comprising the following elements:
(1) a light-transmitting, water-impermeable support, (2) an indicator layer containing a bilirubin extracting composition dispersed in a film-forming hydrophilic polymer binder, and (3) a porous spreading layer, wherein elements (1) to (3) are present in the recited order with respect to each other, said bilirubin extracting composition is hydrophobic to such an extent that it forms at least an emulsion when it is dispersed in neutral water and comprises a hydrophobic oil-soluble primary, secondary or tertiary amine capable of extracting bilirubin and an extraction aid, wherein a dissociating agent for bilirubin is incorporated into the spreading layer or a further layer (4) between the porous spreading layer (3) and the layer containing the bilirubin extracting composition (2) in an amount sufficient to completely dissociate all bilirubin in a sample, and wherein said dissociating agent is caffeine-sodium benzoate.

19. An integral multilayer device for quantitatively determining the amount of bilirubin in an aqueous liquid sample comprising the following elements:
(1) a light-transmitting, water-impermeable support, (2) an indicator layer containing a bilirubin extracting composition dispersed in a film-forming hydrophilic polymer binder, (3) a radiation blocking layer, and (4) a porous spreading layer, wherein elements (1) to (4) are present in the recited order with respect to each other, said bilirubin extracting composition is hydrophobic to such an extent that it forms at least an emulsion when it is dispersed in neutral water and comprises a hydrophobic oil-soluble primary, secondary or tertiary amine capable of extracting bilirubin and an extraction aid, and wherein a dissociating agent for bilirubin is incorporated into the spreading layer or a further layer (5) between the porous spreading layer (4) and the layer containing the bilirubin extracting composition (2) in an amount sufficient to completely dissociate all bilirubin in a sample and layer (2) overlays (1) and is in direct contact therewith.

20. The device for quantitatively determining the amount of bilirubin in an aqueous liquid sample as claimed in claim 19, which further comprises a layer which prevents diffusion of hemoglobin between the porous spreading layer (4) and the bilirubin extracting layer (2).

* * * * *

UNITED STATES PATENT AND TRADEMARK OFFICE
CERTIFICATE OF CORRECTION

PATENT NO. : 4,877,579

DATED : October 31, 1989

INVENTOR(S) : Kenichiro Yazawa, Osamu Seshimoto, Masao Kitajima and Asaji Kondo

It is certified that error appears in the above-identified patent and that said Letters Patent is hereby corrected as shown below:

IN THE CLAIMS

Claim 1, column 13, line 60, delete "layer and 3) the" and insert therefor --layer 3) and the--.

Signed and Sealed this

Third Day of April, 1990

Attest:

HARRY F. MANBECK, JR.

*Attesting Officer*  *Commissioner of Patents and Trademarks*